(12) United States Patent
Krueger

(10) Patent No.: US 12,048,461 B2
(45) Date of Patent: Jul. 30, 2024

(54) MEDICAL TRANSVERSE CONNECTOR HAVING A FLOATING BEARING

(71) Applicant: Aesculap AG, Tuttlingen (DE)

(72) Inventor: Sven Krueger, Trossingen (DE)

(73) Assignee: Aesculap AG, Tuttlingen (DE)

( * ) Notice: Subject to any disclaimer, the term of this patent is extended or adjusted under 35 U.S.C. 154(b) by 318 days.

(21) Appl. No.: 17/611,026

(22) PCT Filed: Apr. 8, 2020

(86) PCT No.: PCT/EP2020/059961
§ 371 (c)(1),
(2) Date: Nov. 12, 2021

(87) PCT Pub. No.: WO2020/233893
PCT Pub. Date: Nov. 26, 2020

(65) Prior Publication Data
US 2022/0313323 A1  Oct. 6, 2022

(30) Foreign Application Priority Data

May 17, 2019 (DE) ..................... 10 2019 113 097.2

(51) Int. Cl.
*A61B 17/70* (2006.01)
*A61B 90/00* (2016.01)

(52) U.S. Cl.
CPC .... *A61B 17/7052* (2013.01); *A61B 2090/031* (2016.02)

(58) Field of Classification Search
CPC .............. A61B 17/7049; A61B 17/705; A61B 17/7052; A61B 17/7043; A61B 17/7041
See application file for complete search history.

(56) References Cited

U.S. PATENT DOCUMENTS

| 6,524,310 | B1 * | 2/2003 | Lombardo ......... A61B 17/7052 606/253 |
| 9,427,263 | B2 | 8/2016 | Larroque-Lahitette et al. |

(Continued)

FOREIGN PATENT DOCUMENTS

| CN | 1444910 A | 10/2003 |
| CN | 102065782 A | 5/2011 |

(Continued)

OTHER PUBLICATIONS

Written Opinion received in International Application No. PCT/EP2020/059961 dated Aug. 3, 2020, with translation, 17 pages.

(Continued)

*Primary Examiner* — Julianna N Harvey
(74) *Attorney, Agent, or Firm* — Christopher A. Rothe; Culhane PLLC

(57) ABSTRACT

A medical cross connector, a corresponding matching torque wrench, and a corresponding medical product set that includes the medical cross connector in combination with at least one bone implant and/or other matching surgical accessory. The medical cross connector includes a cross strut for connecting two longitudinal rods that can be brought into operative engagement for orientation of vertebrae of a spinal column, and at least one clamping head mounted pivotably on the cross strut in an angular bearing. The clamping head has a rod receptacle and a clamping screw. A clamping tooth applies a clamping force to one of the longitudinal rods when the rod is inserted into the rod receptacle. The clamping tooth is mounted pivotably about a pivot axis via a floating bearing. The floating bearing permits a pivoting movement and a lateral movement of the pivot axis of the clamping tooth.

21 Claims, 6 Drawing Sheets

(56) References Cited

U.S. PATENT DOCUMENTS

| | | |
|---|---|---|
| 9,844,398 B2 | 12/2017 | Daniels et al. |
| 2003/0114853 A1 | 6/2003 | Burgess et al. |
| 2005/0261687 A1* | 11/2005 | Garamszegi ........ A61B 17/7032 606/328 |
| 2008/0086134 A1* | 4/2008 | Butler ................ A61B 17/7052 606/103 |
| 2008/0177315 A1 | 7/2008 | Usher |
| 2008/0306538 A1 | 12/2008 | Moore et al. |
| 2009/0105765 A1 | 4/2009 | Strnad |
| 2009/0187217 A1* | 7/2009 | Weiman ............. A61B 17/7052 606/257 |
| 2009/0264926 A1 | 10/2009 | Taylor et al. |
| 2011/0137345 A1 | 6/2011 | Stoll et al. |
| 2013/0165976 A1 | 6/2013 | Gunn |
| 2013/0274807 A1* | 10/2013 | Prajapati ............ A61B 17/7052 606/278 |
| 2014/0088650 A1 | 3/2014 | Taddia et al. |
| 2017/0071637 A1 | 3/2017 | Barrus et al. |
| 2017/0224569 A1 | 8/2017 | Pfeuffer et al. |
| 2017/0281237 A1* | 10/2017 | Murray .............. A61B 17/7004 |
| 2019/0167313 A1* | 6/2019 | Ortiz ................. A61B 17/7049 |

FOREIGN PATENT DOCUMENTS

| | | |
|---|---|---|
| CN | 103948423 A | 7/2014 |
| CN | 203724198 U | 7/2014 |
| CN | 107106395 A | 8/2017 |
| EP | 1302169 A1 | 4/2003 |
| JP | 2015523111 A | 8/2017 |

OTHER PUBLICATIONS

Search Report received in German Application No. 10 2019 113 097.2 dated Jan. 14, 2020, with translation, 14 pages.
Search Report received in International Application No. PCT/EP2020/059961 dated Aug. 3, 2020, with translation, 6 pages.
Notice of Allowance received in Japanese Application No. 2021-568149 dated Nov. 28, 2023, with translation, 2 pages.
Office Action received in Chinese Application No. 202080035839.2 dated Jan. 24, 2024, with translation, 6 pages.
Search Report received in Chinese Application No. 202080035839.2 dated Jan. 17, 2024, with translation, 6 pages.

* cited by examiner

MEDICAL TRANSVERSE CONNECTOR HAVING A FLOATING BEARING

CROSS-REFERENCE TO RELATED APPLICATIONS

This application is the United States national phase entry of International Application No. PCT/EP2020/059961, filed Apr. 8, 2020, and claims the benefit of priority of German Application No. 10 2019 113 097.2, filed May 17, 2019. The contents of International Application No. PCT/EP2020/059961 and German Application No. 10 2019 113 097.2 are incorporated by reference herein in their entireties.

FIELD

The present disclosure relates to a medical cross connector for connecting two longitudinal rods, in particular so-called spinal rods, which can be brought into operative engagement preferably with pedicle screws or similar bone implants, as used for orientation vertebrae of a spinal column. The present disclosure further relates to a corresponding torque wrench. In addition, a corresponding medical product set comprising the medical cross connector in combination with at least one bone implant such as a pedicle screw, with a surgical instrument, and/or with another matching surgical accessory is proposed.

BACKGROUND

In the prior art of spinal surgery, it is known to surgically use medical cross connectors for connecting spinal rods for the purpose of orientation, repositioning, distraction, stabilization, etc. of vertebrae of a, in particular human, spinal column. The respective spinal rod usually has at least one pedicle screw in active engagement with a vertebra. For this purpose, the pedicle screw is screwed as a bone implant into a pedicle of the vertebra, i.e. into a pedicle region between the vertebral body and the vertebral arch. Medical indications in which medical cross connectors are used by a user such as an orthopedic or reconstructive surgeon during spinal surgery include degenerative disc disease, trauma (including fractures or dislocations), post-traumatic kyphosis or lordosis, tumors, spondylolisthesis, spinal stenosis, deformities (scoliosis, kyphosis and/or lordosis), pseudarthrosis after unsuccessful spinal surgery, symptomatic cervical spondylosis, instability after surgical intervention due to the above indications, reoperations due to failure of a previous fusion, etc.

The aim is to minimize the time required by the surgeon for the insertion of the cross connector in order to minimize the operative burden on the patient and to optimally support the patient's healing and recreation. Since the adjustment of the cross connector to the anatomical situation to be treated and thus to the three-dimensional positioning of the spinal rods is particularly time-consuming, there is a need for cross connectors that can be inserted and adjusted quickly and flexibly.

EP 1302169 A1 discloses a medical cross connector for two spinal rods. Thereby, a first connecting piece of the cross connector has a first clamping element and a second clamping element and a fastening element, which is configured to hold the first clamping element and the second clamping element firmly together in order to grip a spinal rod. In this regard, at least a portion of the at least one multiaxial joint is disposed between the first clamping member and the second clamping member such that when the fastening member holds the first clamping member and the second clamping member together, the portion is squeezed to prevent rotation of the at least one multiaxial joint. In other words, by actuating a clamping screw accessible to the surgeon as the fixing element, on the one hand, the spatial position of the multiaxial joint arranged between two spinal rods to be connected and, on the other hand, one of the two spinal rods are fixed simultaneously (see also FIG. 3 of EP 1302169 A1). So, the rod clamping and the angular bearing of a cross strut of the cross connector are fixed in one move.

However, there are some disadvantages with the prior art solution presented above: First, the clamping of the spinal rod builds up in anterior and posterior directions with respect to the patient, which must be considered anatomically disadvantageous and non-atraumatic, respectively. Last but not least, a healing prognosis must therefore also be more negative. Secondly, the positioning of the clamping screw in the direct vicinity of the spinal rod to be clamped results in a disadvantageous extension of the surgical access in a lateral direction with respect to the patient.

Another disadvantage is that the parallel arrangement of the two different clampings, i.e. the clamping of the spinal rod on the one hand and the clamping of the angular bearing of the cross strut on the other, means that the corridor in which both clampings can be adequately fixed in the same movement directly via the clamping screw is narrow. This has the serious disadvantage that the manufacturing tolerances of the individual mechanical elements of the cross strut must be very small. Ultimately, both of the two different clampings have to be reliably represented in order to fulfill the basic function of a retainer that is also secure over the long term. Thus, the production of such a known cross connector necessarily turns out to be complex and cost-intensive.

Furthermore, although the known cross connector theoretically permits the clamping of different rod diameters, a variability of the rod diameter is likely to be very small in this design due to the above-mentioned connection of the mechanics of the two clampings.

SUMMARY

Thus, the aim of the invention is to provide a medical cross connector for connecting two spaced longitudinal rods of a bone implant, preferably a spinal implant, which overcomes the disadvantages of the prior art set forth above. First of all, a quick, flexible and long-term reliable insertion and adjustment to the anatomical situation as well as to different rod diameters should be made possible. In particular, an additional task is to provide the surgeon with a cross connector suitable for largely atraumatic insertion. In this respect, the constructive design of the cross connector should require a smaller operative access area as well as a smaller posterior design in order to enable minimal retraction or impairment of anatomical structures such as surrounding tissue or nerve roots, etc. The more structures that can be left intact during the surgical insertion, the more a physiological environment is created that promotes healing. A still further task is to create a more favorable design with regard to required dimensional tolerances and fits of the cross connector to be manufactured.

The medical cross connector as a first aspect of the present disclosure comprises a cross strut for connecting two longitudinal rods that can preferably be brought into operative engagement with pedicle screws or similar bone implants. In particular, the device can be used for orientation (positioning) of vertebrae of a spinal column. Further, the medical cross connector comprises at least one clamping head being mounted pivotably on the cross strut in an angular bearing. This has a trough-shaped rod receptacle and a clamping screw. This element of the clamping head or cross connector, respectively, serves to receive and clamp a longitudinal rod in such a way that longitudinal rods of different diameters can be gripped by the cross connector in a flexible manner and in the form of a long-term secure holder. The clamping screw, when actuated, applies a clamping force to the at least one longitudinal rod inserted in the rod receptacle by means of a clamping tooth mounted pivotably about a pivot axis via a rocker bearing. Due to this, the clamping screw fixes an angular position of the angular bearing between the clamping head and the cross strut at the same time or with a time offset. According to the invention, the rocker bearing is configured as a floating bearing. In this case, the floating bearing permits a pivoting movement and a lateral movement of the pivot axis of the clamping tooth which lateral movement is generated due to clamping forces between the longitudinal rod and the clamping tooth. The lateral movement thus generated acts on the angular position of the angular bearing between the clamping head and the cross strut in a fixing and/or locking manner.

Thus, according to the invention, via the floating rocker bearing, the longitudinal rod clamping and the angular bearing of a cross strut of the cross connector are not caused and/or fixed in one go by means of the actuation of the clamping screw, but successively. The fixing and/or locking of an angular position, which the clamping head and the cross strut assume at the moment of fixing and/or locking with respect to each other, takes place as a result of the lateral movement, which in turn is generated due to clamping forces.

The lateral movement of the center of the rocker bearing can take place along a path that is structurally configured for this purpose in the clamping head. In particular, the path leading the lateral movement is aligned along the longitudinal direction and/or a longitudinal direction component of the clamping head or the cross connector, respectively, for example along an elongated hole provided longitudinally or at an angle. Thereby, the elongated hole can have not only a linear but also a curved, e.g. asymptotic, course. Also a special mapping of a specific curve function over the longitudinal direction is conceivable.

In other words, on the one hand, the longitudinal rod clamping at the longitudinal rod-side end of the cross connector and, on the other hand, the angulation of the cross connector, at the end of the cross connector opposite the longitudinal rod clamping, that is at the end possibly facing the spinal column, are "connected in series", so to speak. This is intended to mean that the two clamps lie in a force flow.

This is realized by the floating design of the bearing of the pivot axis (in the transverse direction of the cross connector) of the clamping tooth being mounted pivotably in the rocker bearing. The pivot axis of the clamping tooth experiences a transverse force component at least in the longitudinal direction of the cross connector as soon as the clamping tooth comes into contact with the longitudinal rod. Then, as a counterforce, the force resistance to the longitudinal rod builds up depending on its degree of hardness or deformability, resp., and thereby resulting deformation. In the resulting equilibrium of forces, this transverse force component thus corresponds to the force that leads to clamping of the rod.

Via the floating bearing, the counterforce of this transverse force component of the rocker bearing, which acts on the pivot axis of the clamping tooth, is transmitted to the clamping, fixing or locking mechanism, resp., of the angular bearing. For example, the force is transmitted from the rocker bearing to the angular bearing via an intermediate element of the clamping head, preferably via a U-shaped fork mount. There, this counterforce thus causes a fixing and/or locking of the angulation of the clamping head to the cross strut or vice versa, resp., in its angular bearing. In particular, surface pressing forces in equilibrium with the counterforce can act on surface portions of the angular bearing in an angle-fixing and/or angle-locking manner.

Thus, in a first force flow phase, the clamping screw of the rocker bearing is configured to rotate the clamping tooth as a first clamping means in the direction towards the longitudinal rod about the pivot axis as a first axis of rotation until clamping of the longitudinal rod along a contact line between clamping tooth and longitudinal rod is achieved. And then, in a second force flow phase, to rotate the clamping tooth about the contact line as a second axis of rotation by its further actuation in order to move the pivot axis in the direction away from the longitudinal rod along a path length. The path is configured in the clamping head to permit and/or represent a lateral movement of the rocker bearing. Thus, the rocker bearing is configured as a floating bearing. The lateral movement generated in the course of setting a force equilibrium on the rocker bearing with gripped longitudinal rod in turn builds up the clamping forces acting on the clamping of the angular bearing. A further equilibrium of forces of the clamping forces is established in the angular bearing, which causes a fixing and/or locking of the angular position of the angular bearing.

It is not relevant in the sense of the invention that the longitudinal rods have a cylindrical or quasi-cylindrical shape. Thus, the term longitudinal rod as used herein does not refer only to elongated shapes with a constant round cross-section, but also includes any longitudinal member with a cross-section that varies along its longitudinal axis and/or with a cross-section that has a non-circular shape, for example, an oval, rectangular, U-shaped, T-shaped, I-shaped, convex and/or concave shape. In a broader sense, the term longitudinal rod may also comprise a support plate, preferably a plate having along at least a portion of its outer periphery an outer radius of its outer edge forming a semi-cylindrical rod.

Preferably, the angular bearing of the medical cross connector is configured to be polyaxial. This means that the angular position between the clamping head and the cross strut is changeable and/or fixable not only uniaxially, that is in a single axial direction, such as with a hinge joint as an example of a uniaxial joint. Rather, in this preferred embodiment, the angular position can be changed and/or fixed in at least two, preferably three axial directions. The angular position taken by the polyaxial angular bearing according to two or three planes in space determines the angular position between the longitudinal rod and the cross strut that is ultimately to be fixed and/or locked, so as to permit more spatial positions of the longitudinal rod and the cross strut relative to each other. The advantage of this is that the cross connector can be better and more flexibly adjusted to the anatomical situation. The occurrence of unfavorable tensions or twistings, resp., in the cross connector and/or in the surrounding overall system in which the cross connector is inserted is thus better avoided.

Preferably, a three-axis joint is configured in the form of a ball joint angular bearing between the clamping head and the cross connector. A three-axis joint has three degrees of freedom with regard to the three axial directions of the angular bearing, namely in the longitudinal, vertical and transverse directions, and in each case in the positive and/or negative axial direction. The basically unlimited mobility of the ball joint is limited only by the structural elements of the angular bearing, which perform the bearing function and/or provide guidance. Such a particularly preferred embodiment as a triaxial joint permits angularization according to ideally almost complete three degrees of freedom. This permits internal compensating movements, with respect to the cross connector itself and/or the surrounding overall system, in all three planes of space before the angular position is determined by the user such as a surgeon.

Preferably, the polyaxial angular bearing is configured to be preloaded and/or preloadable by means of a spring element or preloading element, respectively. In this regard, a preferred embodiment of the spring element relates to a tension and/or compression spring integrally formed in a component of the rocker bearing. Preferably, the component of the rocker bearing is thereby the intermediate element of the clamping head, particularly preferably in the U-shaped fork mount. Alternatively and/or cumulatively, the spring element is preferably arranged to cause a preceding snap onto the longitudinal rod for clamping the longitudinal rod.

Preferably, the clamping screw is reversibly releasable. This permits the user to readjust after a preliminary clamping. Alternatively or cumulatively, the clamping screw is configured as a self-locking fastening element. This additionally secures the clamping against unintentional loosening and thus to a particular extent against undesired failure of the cross connector.

Preferably, the clamping tooth is adjustable and/or adjusted to be differently shaped and/or dimensioned for different diameters of the longitudinal rod. It is further preferred that the clamping tooth is configured for diameters of the longitudinal rod in the interval of 3 to 7 mm, particularly preferably for the cervical or neck region in the interval of 3.5 to 4.0 mm and/or for the lumbar or lumbar vertebrae region in the interval of 5.5 to 6.0 mm. This means that different clamping teeth can be set up in the clamping head in a modular fashion. In this way, the flexibility of the cross connector can be further increased to meet specific needs in accordance with the overall anatomical situation or the overall system.

Preferably, components or, resp., elements of the cross connector and/or the longitudinal rod are made of a biocompatible material such as a ceramic. Particularly preferably, at least one of or all of the components or, resp., elements of the cross connector and/or the longitudinal rod is made of a titanium alloy. The longitudinal rod may be formed of a soft and/or hard material.

As a second aspect of the present disclosure, a torque wrench which is suitably adapted to a clamping screw of a medical cross connector according to the invention is proposed. Therein, the corresponding torque wrench is adjustable and/or adjusted to apply a minimum and/or maximum permissible torque. This is configured so that the clamping force applied to the at least one longitudinal rod inserted into the rod receptacle does not fall below a minimum permissible first force limit and/or does not exceed a maximum permissible second force limit. Alternatively or cumulatively, this is configured so that the opposing force caused by the lateral movement acting in a fixing and/or locking manner on the angular position of the angular bearing between the clamping head and the cross strut does not fall below a minimum permissible third force limit and/or does not exceed a maximum permissible fourth force limit. Alternatively or cumulatively, the torque for tightening the clamping screw for connecting the longitudinal rods in the cervical or neck region is preferably 2.3 to 3.3 Nm, particularly preferably 2.8 Nm, and/or in the lumbar or lumbar vertebrae region is preferably 4.5 to 5.5 Nm, particularly preferably 5.0 Nm. The torque wrench can be configured to accommodate a lever handle or, resp., screwdriver with an internal thread or, resp., screw driving profile, for example in the form of a hexagon or, resp., an internal hexagonal round or a screw driving profile in a polygonal shape, such as the screw drive configuration available under the federally registered trademark TORX®.

Such a torque wrench has the particular advantage that the manufacturer ensures that the clamping forces to be set by the user by operating the clamping screw on the rocker bearing and then on the angular bearing are within advantageous limits or, resp., intervals. The influence of the manual force of an individual user such as an operator on the rod clamping as well as on the fixing and/or locking of the angular position is eliminated or, resp., a person-dependent dispersion is avoided by using a suitable torque wrench.

Preferably, the corresponding torque wrench is thereby adjustable and/or configured differently for different diameters of the longitudinal rod, preferably at preset intervals. This permits the user an individual, yet manufacturer-guided, intuitive setting of the desired torque and the resulting clamping forces.

As a third aspect of the present disclosure, a further medical product set, preferably a pedicle screw and hook system for stabilization and/or correction of the spinal column, comprising a medical cross connector according to the invention is proposed. In this regard, a combination of the medical cross connector comprises at least one longitudinal rod, preferably a plurality of longitudinal rods, preferably in an assembly of the longitudinal rods of straight and/or curved shape and/or according to different sizes and/or degrees of hardness and/or materials; and/or a bone implant such as a poly- and/or monoaxial screw; and/or a pedicle hook; and/or a surgical instrument such as a rod insertion forceps, an implant holder, a distractor or the like. Such a product set is considered particularly useful by treating physicians and preparatory clinical staff. In particular, such a product set supports customized surgical preparation. Furthermore, there are advantages for the logistic processes in the manufacturer's as well as in the clinical area.

The product set according to the third aspect of the disclosure may further comprise a torque wrench according to the second aspect of the disclosure.

Finally, it should be noted that the medical cross connector according to the invention is not limited to use solely in spinal surgery orientation of vertebrae of a spinal column using spinal rods. The invention is equally advantageous for similar medical uses, particularly for the variety of surgical, maxillofacial, sports medicine, orthopedic, reconstructive, curative and/or rehabilitative situations and procedures. In particular, the same basic medical principles and therapeutic goals underlie fracture treatment in the extremities, for example, a broken leg or foot, and spinal fusion.

In this respect, the present terms of the longitudinal rod or, resp., the corresponding cross connector include all medically or, resp., specifically useful designs and/or size dimensions and/or materials for this purpose. For example, in the field of plastic-aesthetic and/or reconstructive jaw surgery or, resp., orthodontics, a comparatively smaller scale of the longitudinal rod (in the case of a spinal rod, such a rod has a preferred diameter of 3 to 7 mm) or, resp., of the corresponding cross connector according to the invention is to be assumed. Accordingly, a preferred embodiment, namely one adapted or dimensioned in particular in scale to the other anatomical situation, in particular one miniaturized to the present ratio factor, is not to be excluded but is encompassed by the present disclosure.

BRIEF DESCRIPTION OF THE DRAWING FIGURES

Figure 5A:
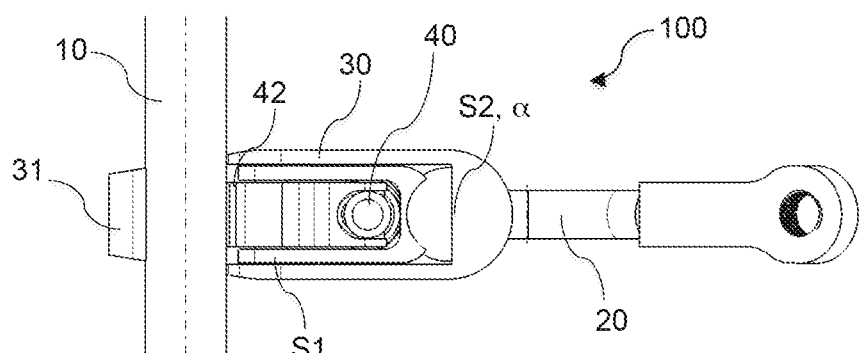
Figure 5B:
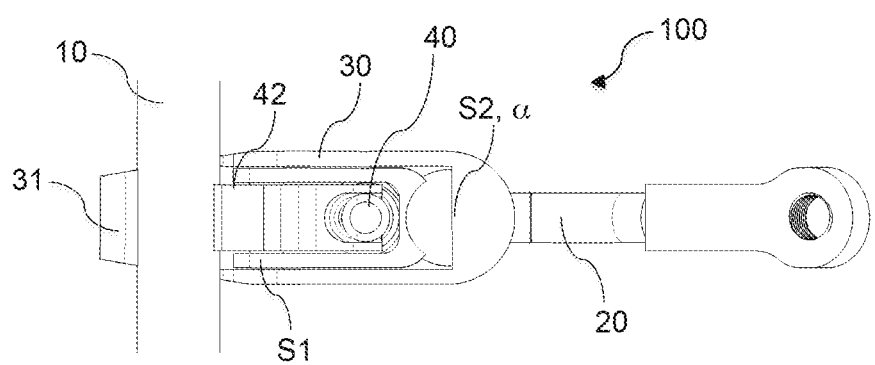
Figure 5C:
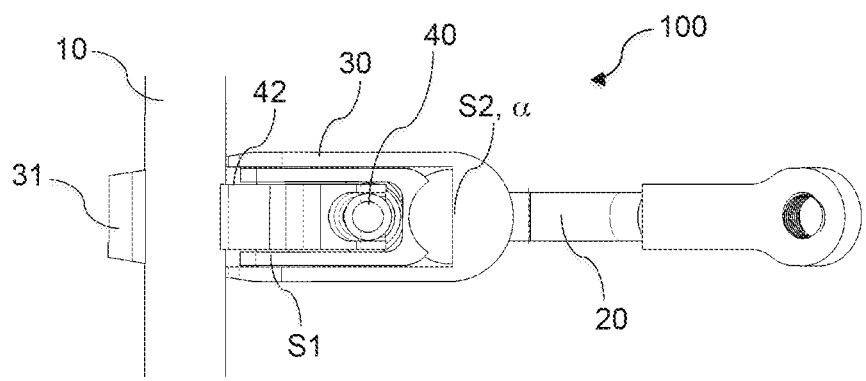
Figure 6A:
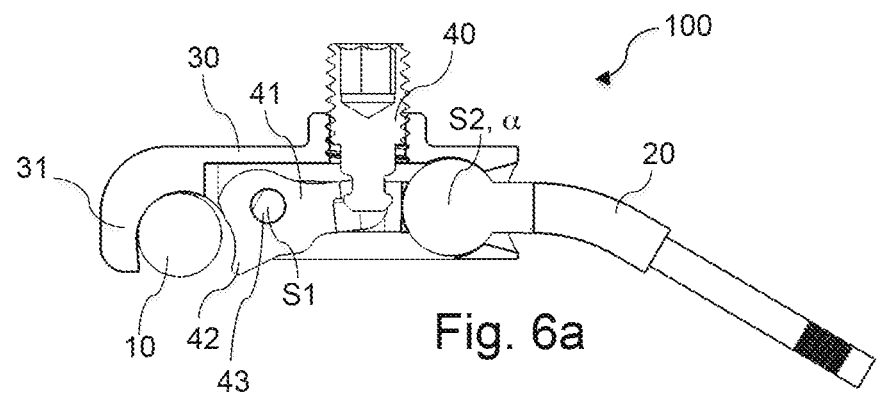
Figure 6B:
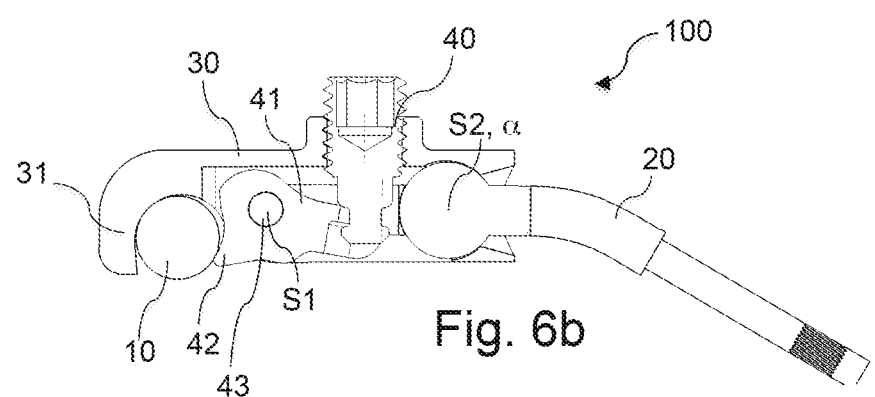
Figure 6C:
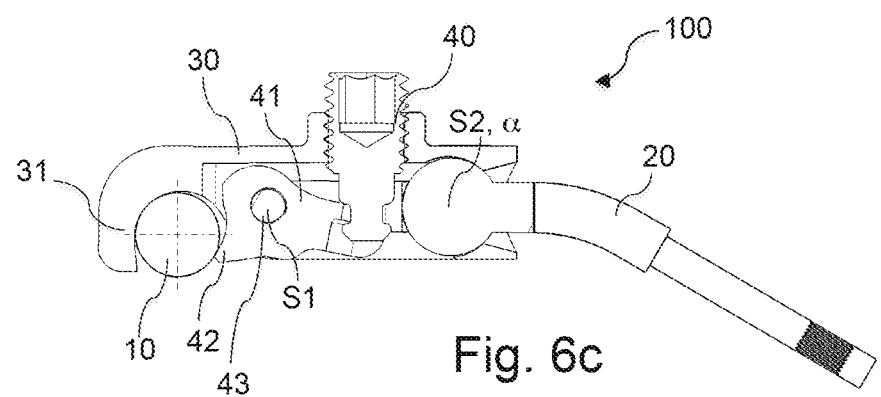
Figure 7:
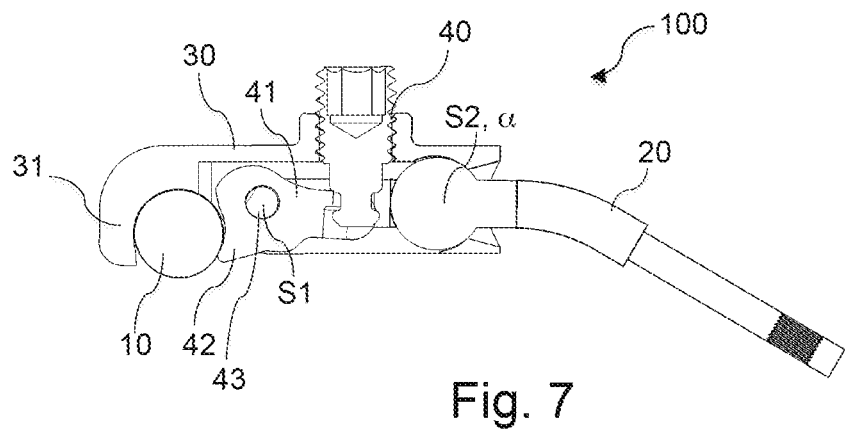
Figure 8:
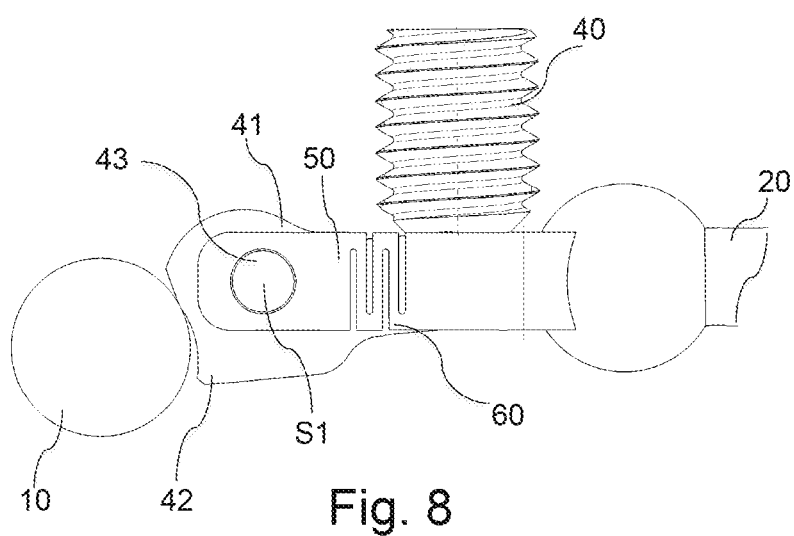
Figure 9:
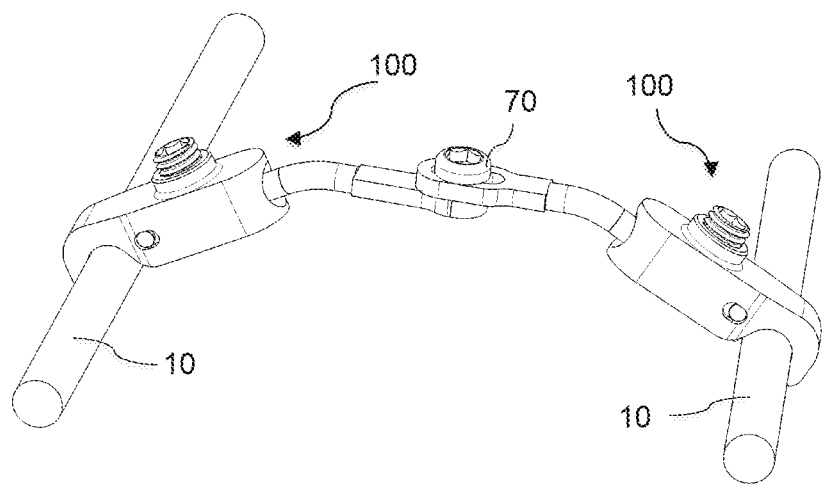
Figure 10:
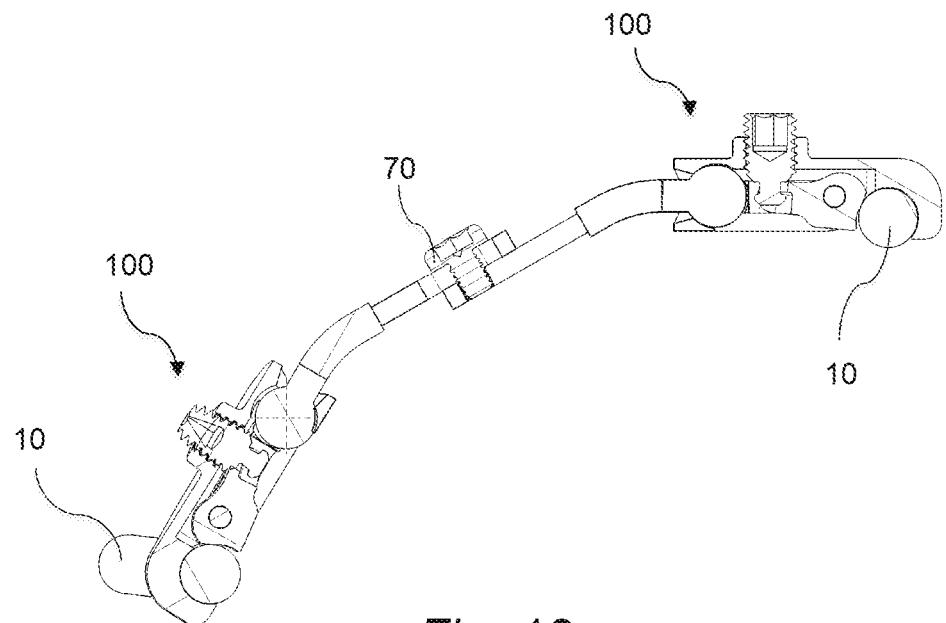

FIGS. 5a to 5c each show a top view according to a second embodiment of the medical cross connector in a functional sequence at three points in time [a) open; b) rod-clamping; c) angle-fixed], illustrating in particular the functioning of the floating rocker bearing of a clamping tooth clamping a first longitudinal rod, the floating rocker bearing acting on the angle-fixing of the angular bearing;

FIGS. 6a to 6c each show a front view in longitudinal section according to the second embodiment of the medical cross connector at the respective three points in time of the above mentioned FIGS. 5a to 5c;

FIG. 7 is a front view in longitudinal section according to the second embodiment of the medical cross connector at the third time point of an angle-fixed (angle-locked) state by means of a, compared to the first longitudinal rod in FIG. 6c, thicker second longitudinal rod;

FIG. 8 is a detail of a front view in longitudinal section according to a preferred variation of the second (or, resp., the first) embodiment of the present invention regarding a resilient design of the fork holder;

FIG. 9 is a perspective view of a centrally coupled arrangement of two cross connectors according to the second embodiment; and FIG. 10 is a front view in (partial) longitudinal section of a centrally coupled arrangement of two cross connectors according to the second embodiment.

DETAILED DESCRIPTION

Hereinafter, a first embodiment of the present disclosure is described on the basis of the corresponding FIGS. 1 to 4. From this, further details, features and advantages of the invention will be apparent.

Figure 1:
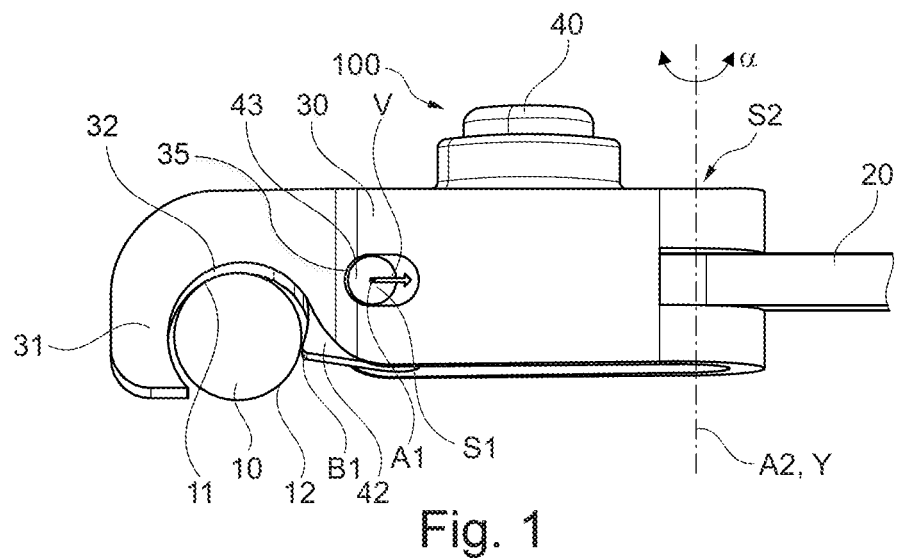
FIG. 1 is a (slightly perspective) front view according to a first embodiment of the medical cross connector according to the present disclosure, into which a longitudinal rod is clamped.

FIGS. 1 to 4 show different views according to a first embodiment of a medical cross connector 100 according to the invention. FIG. 1 shows a slightly perspective front view of the medical cross connector 100, in which a spinal rod 10 is clamped as a longitudinal rod (left in FIG. 1). To begin with, the medical cross connector 100 includes a cross strut 20 (right in FIG. 1) for medially connecting two spinal rods 10, the second of which is not included in the illustration. In most cases (not shown), two cross connectors 100 are coupled together to form an arrangement medially with respect to the patient, i.e., above the center of the spinal column (for comparison, see also FIGS. 9 and 10 for the second embodiment). In this respect, the views of all FIGS. 1 to 4 are interrupted, which is indicated by the wavy line according to the representation standard for technical drawings (on the right in FIGS. 1 to 4). This bridges across the center of the spinal column in a lateral direction with respect to the patient, that is, virtually in the direction of the ribs. The individual cross connector is then also integrated into an overall system stabilizing the spinal column for orientation of the individual vertebrae. The respective spinal rods 10 or support plates are brought into active engagement with the vertebrae in the course of a spinal surgery operation by means of pedicle screws in the manner of a bone implant (not shown).

Figure 3:
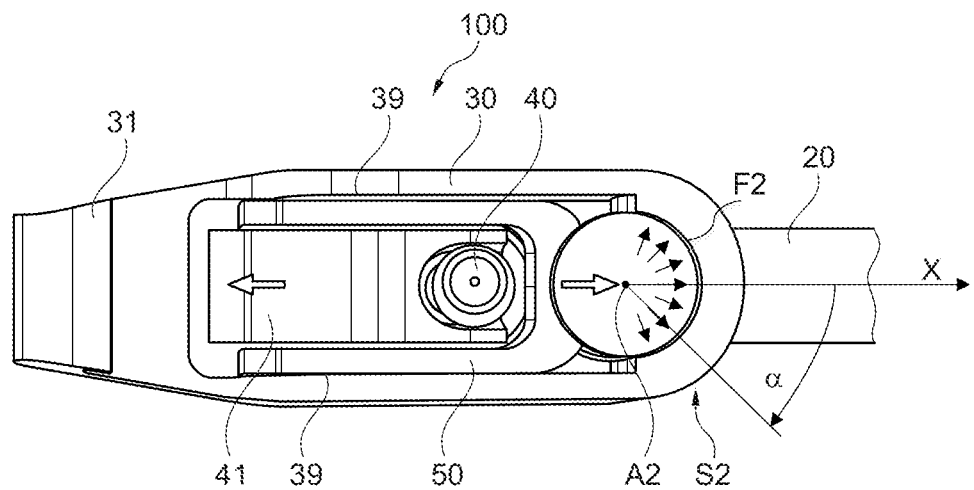
FIG. 3 is a top view according to the first embodiment of the medical cross connector, illustrating in particular the force flow from the floating rocker bearing to the angular bearing.
Figure 4:
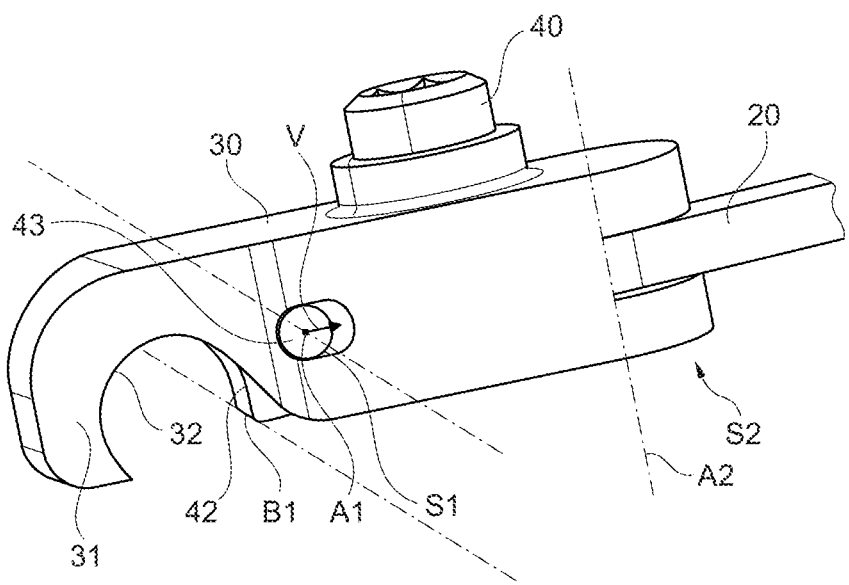
FIG. 4 is a second perspective front view according to the first embodiment of the medical cross connector (without longitudinal rod)

Further, the cross connector 100 includes a housing-shaped clamping head 30 having a trough-shaped rod receptacle 31 (shown at left in FIGS. 1, 3 and 4; provided at the lateral head side of the cross connector 100). The trough-shaped rod receptacle 31 has an inner bearing surface 32 formed with a shape approximately complementary to a spinal rod 10 to be gripped. Here, the inner bearing surface 32 is formed with a somewhat wider radius than the radius of the spinal rod 10 to extend in a cup-like manner and is configured like a hook jaw to engage a cylindrical outer first surface portion 11 of the spinal rod 10. A clamping tooth 42 engages as a counter element on an approximately diametrically opposite second surface portion 12 of the spinal rod 10. For this purpose, the clamping tooth 42 is mounted via a rocker bearing S1 provided in the clamping head 30 so as to be pivoting about a pivot axis A1. To hold the spinal rod 10, the clamping tooth 42 can be pressed against it by a pivoting movement (in FIG. 1: clockwise) about the pivot axis A1, forming a contact line B1 between the convex tip of the clamping tooth 42 and the second surface portion 12 of the spinal rod 10. Here, the contact line B1 is substantially parallel to the pivot axis A1.

To form the pivot axis A1, a cylinder pin 43 is received in the transverse direction Z in two elongated holes 35 provided on opposite side surfaces of the clamping head 30. Due to the mounting of the cylinder pin 43 in the elongated holes 35, the rocker bearing S1 is configured as a floating bearing. In this respect, the floating bearing enables a relative movement or, resp., an evasive movement of the cylinder pin 43 constituting the pivot axis A1 along the elongated holes 35 for describing a lateral movement vector V of the pivot axis A1 in the rocker bearing S1.

The inner angularity of the cross connector 100 is changeable in the degree of freedom of a hinge joint S2 as a uniaxial angular bearing (shown on the right in FIGS. 1 to 4). For this purpose, in the hinge joint S2 the clamping head 30 is mounted pivotably on the cross strut 20. The angular position a determining the angulation between central body axes of the clamping head 30 and the cross strut 20 as angular legs is changeable about a single hinge axis A2 as axis of rotation in the hinge joint S2. In the example shown in FIG. 1, the joint axis A2 coincides with the vertical direction Y of the clamping head 30. Thus, the angular position a is pivotable in a plane spanned by the longitudinal direction X and the transverse direction Z (see FIG. 2).

Further, the cross connector 100 includes a clamping screw 40 (shown at the top of FIG. 1). The clamping screw 40 is used to actuate the clamping mechanisms of the cross connector 100 by a user, for example by a spine surgeon from the posterior side. Initially, by advancing the clamping screw 40, a fastening of the cross connector 100 to the spinal rod 10 is effected by means of the pivotably mounted clamping tooth 42. And further, by redirecting (deflecting) the flow of force, a fixing of an inner angular position of the cross connector 100, i.e. of the angular position a, is caused. In between, the user can once again more precisely align and/or readjust the hinge joint S2 to a correct, tension-free or, resp., desired position and fix and/or lock a current angular position a by means of a further actuation of the clamping screw 40. Overall, in a continuous or, resp., only briefly interrupted locking process, the user can further screw the clamping screw 40, ideally moderately, into the clamping head 30, having initially already caused (effected) the clamping of the spinal rod 10.

For this purpose, the floating rocker bearing S1 permits a lateral movement (vector) V of the pivot axis A1 of the clamping tooth 42, the lateral movement (vector) V being generated due to clamping forces between the longitudinal rod 10 and the clamping tooth 42, which is guided and/or limited by the elongated hole 35. This is accompanied by an evasive movement of the pivot axis A1 about the contact line B1 formed between the convex tip of the clamping tooth 42 and the second surface portion 12 of the spinal rod 10. In other words, the cylinder pin 43 pushes away from the longitudinal rod 10 via the clamping tooth 42 supported by means of it along the contact line B1 to perform an evasive movement in the form of the lateral movement vector V along the elongated hole 35. Thus, the cylindrical pin 43 of the floating rocker bearing S1 shifts by the lateral movement vector V, that is away from the longitudinal rod 10 and towards the hinge joint S2. This mechanism, in turn, acts to fix and/or lock the angular position a of the hinge joint S2 between the clamping head 30 and the cross strut 20 (see also force arrows shown symbolically in FIG. 3).

Figure 2:
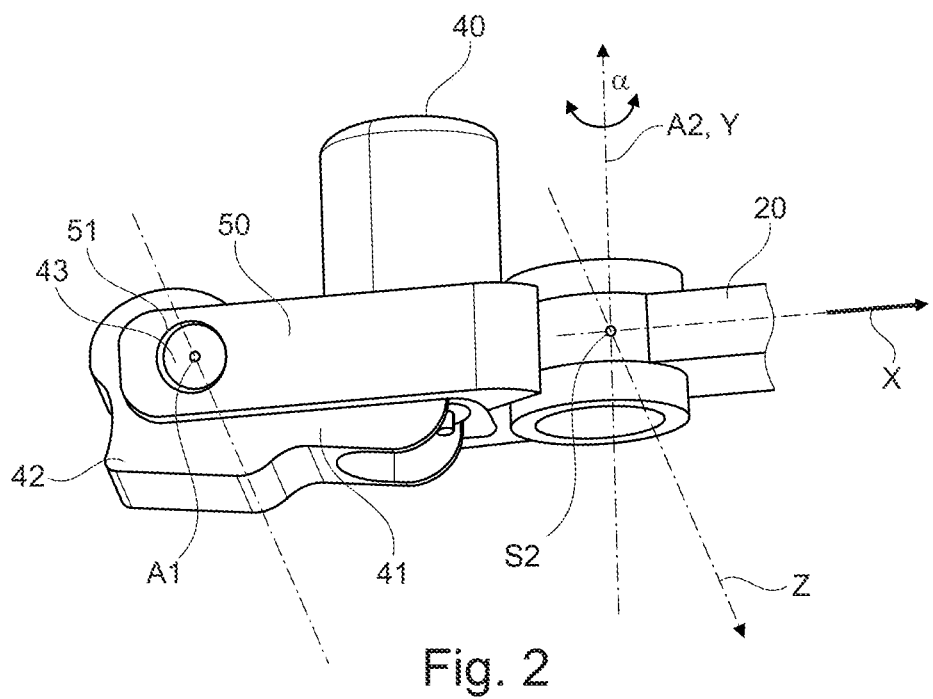
FIG. 2 is a first perspective front view according to the first embodiment of the medical cross connector, for illustration of the clamping tooth being mounted pivotably via the rocker bearing illustrated without the housing of the clamping head.

FIGS. 2 and 3 illustrate the design details inside the clamping head 30 of the cross connector 100, which implement the interaction or, resp., flow of forces within the floating rocker bearing S1 up to the hinge joint S2. That is, FIG. 3 shows a top view according to the first embodiment of the medical cross connector 100, wherein in particular arrows drawn centrally in the arrangement are intended to indicate the force flow of the clamping forces. Again, FIG. 2 shows a first perspective front view according to the embodiment of the medical cross connector 100, which is shown without an outer housing of the clamping head 30 for the purpose of illustrating the clamping tooth 42 that is mounted pivotably via the rocker bearing S1. Thus, the view of the pivot-mounting of the clamping tooth 42 is unobstructed, the pivot-mounting being implemented by means of the cylinder pin 43 enclosed in two cylinder bores 51 on respective opposite sides of a fork holder 50 of U-shaped design. The fork holder 50 is arranged on the outside of a pressing element 41 of the clamping tooth 42 inside the clamping head 30 and movable there between. Thereby, the clamping tooth 42 or, resp., the pressing element 41 is enclosed in a U-shape by the fork holder 50 on a front side facing away from the rod receptacle 31 and facing the hinge joint S2. On the other hand, the rod receptacle on the head side is not enclosed by the fork holder 50 or, resp., is left free by the latter. During a movement of the cylinder pin 43 supporting the clamping tooth 42 or, resp., the pressing element 41 along the lateral movement vector V, the fork holder 50 is movably guided in the clamping head 30 at its outer side surfaces by corresponding inner surfaces 39, 39 of the clamping head 30. Due to the lateral movement vector V of the fork holder 50, angle-fixing clamping forces are generated in the transition to the cross strut 20 in the area of the hinge joint S2, as indicated by means of thin arrows as surface pressing forces in the convex surface portion F2 of the hinge joint S2 facing the cross strut 20. As a result, the clamping screw 40 finally fixes and/or locks the angular position a of the hinge joint S2 between the clamping head 30 and the cross strut 20.

FIG. 4 shows a more perspective front view of the medical cross connector 100 compared to FIG. 1, but without a clamped spinal rod 10. To avoid repetition, reference is made to the explanations on FIG. 1.

In the following, a second embodiment of the present invention will be described with reference to FIGS. 5a to 7, wherein essentially only the constructive features different from the first embodiment will be discussed. With respect to all other features and modes of operation, reference is made to the foregoing description of the figures.

In the second embodiment, the uniaxial angular bearing known from the first embodiment of a cross connector 100, configured as a hinge joint S2, is replaced by a polyaxial angular bearing between the clamping head 30 and the cross strut 20, configured as a ball joint S2.

Specifically, the functional operation of the two clamping actions described above is illustrated in the sequence of three connected FIGS. 5a to 5c and FIGS. 6a to 6c, respectively, which correspond to three different points in time. Here, FIGS. 5a to 5c show a top view of the cross connector 100 from a side facing away from the clamping screw 40, whereby an inserted spinal rod 10 is also shown. Correspondingly, FIGS. 6a to 6c show the same three points in time in the illustration as a longitudinal section through the cross connector 100. The spinal rod 10 has a comparatively smaller diameter in all FIGS. 5a to 6c (for comparison, see FIG. 7 with an alternative spinal rod 10 of a comparatively larger diameter). Thus, the mechanism or the kinematics of the successive clamping actions described above, first of a spinal rod 10 inserted into the cross connector 100 by means of the clamping tooth 42 mounted in the floating rocker bearing S1 and then with respect to the three-dimensionally pivoting angular position in the ball joint S2, is/are shown at three distinctive points in time: Namely, a first point in time, as shown in FIGS. 5a and 6a, respectively, marks an initial position before the clamping screw 40 is screwed in and/or actuated in which the spinal rod 10 is loosely embraced by and/or placed in the rod receptacle 31. A subsequent second time point, as shown in FIGS. 5b and 6b, respectively, marks an initial clamping position. In this, the clamping tooth 42 has come into initial contact with the spinal rod 10 by further actuation of the clamping screw 40 to pivot the pressing element 41 clockwise, so that a clamping force has built up between the clamping tooth 42 and the spinal rod 10. A third point in time, as shown in FIGS. 5c and 6c, respectively, marks a position in which a force flow to the locking mechanism of the ball joint S2 occurs via the evasion of the floating rocker bearing S1 sideways away from the clamped spinal rod 10. Thereby, the force flow exerts an angle-fixing effect on the spatial angular position a in which the ball joint S2 is currently located at the time.

FIG. 7 corresponds to FIG. 6c described above and likewise shows the cross connector in longitudinal section at the third point in time at which the angle-fixing or, resp., angle-locking effect on the ball joint S2 is achieved. In contrast to FIG. 6c, in FIG. 7 the final situation with an alternative spinal rod 10 of a comparatively larger diameter is shown. In this respect, the thicker spinal rod 10 in FIG. 7 is almost completely in contact with a radius around its cross-sectional circumference being approximately complementary to the rod receptacle 31. The comparison of the two figures illustrates that, due to the configurations of the clamping by means of the clamping tooth 42 mounted in the floating rocker bearing S1, it is well possible to securely embrace and to clamp spinal rods 10 of different diameters and, at the same time, to present a good angle-fixing clamping effect on the ball joint.

In the following, with reference to FIG. 8, a preferred variation of the second (or, resp., first) embodiment of the present invention is described. Thereby, attention is to be paid essentially only to the constructive feature, particularly embodied with respect to the second embodiment, of a ball joint S2 preloaded and/or preloadable by means of a spring element 60. In this specific embodiment, the spring element is recognizable as a mechanical compression spring integrally cut into the U-shaped fork mount 50 (for comparison, see also FIG. 2) with a meandering contour, for example by means of a cutting production, a sawing or wire erosion process, etc. With regard to all further features and functionalities, reference is made to the above figure description for the second embodiment (ball joint S2, i.e. polyaxial) or, resp., for the first embodiment (hinge joint, i.e. uniaxial), respectively.

FIGS. 9 and 10 show an arrangement of two cross connectors, which are shown in this illustration according to the second embodiment, in order to illustrate the particularly high three-dimensional degrees of freedom of the two respective ball joints. FIG. 9 shows a perspective view (as from posterior). Whereas, the corresponding FIG. 10 shows a slightly perspective longitudinal section. Therein, the direction of view is parallel to the longitudinal axis of the second spinal rod 10 shown on the right, in cross-section (i.e. longitudinal axis orthogonal to the paper surface), or, resp., slightly angled, that is only approximately parallel to the longitudinal axis of the first spinal rod 10 shown on the left, in a slightly perspective top view, in cross-section.

With respect to the spinal column (not shown) of a patient, the elongated arrangement of the two cross connectors 100 is to be thought of as an arrangement which is coupled medially with respect to the patient, i.e., above the center of the spinal column. The central or, resp., medial coupling of the two cross connectors 100 to each other is achieved by means of a cross connector-central connection 70. Thereby, the lateral course of the arrangement, from the first spinal rod 10 (shown on the left) across the two cross connectors 100 to the second spinal rod 10 (shown on the right), forms an anatomically favorable, curved arch over the center of the spinal column (in FIG. 9, the center of the spinal column can be thought of as being arranged below the cross connector-central connection 70).

Also in this case, all advantages of the first embodiment can be realized. For the sake of completeness, however, it should be noted that a not dissimilar picture would result for an arrangement of two cross connectors of the first embodiment, although fewer degrees of freedom for the overall angulation of such an arrangement would apply. It is readily apparent to those skilled in the art that, in principle, two cross connectors of different embodiments can be coupled via the cross connector-central connection 70.

The invention claimed is:

1. A medical cross connector comprising:
   a cross strut for connecting two longitudinal rods configured for operative engagement for orientation of vertebrae of a spinal column; and
   a clamping head mounted pivotably on the cross strut in an angular bearing and having a trough-shaped rod receptacle and a clamping screw,
   wherein the rod receptacle is configured to receive one of the two longitudinal rods in the rod receptacle,
   wherein the clamping screw, when actuated, applies a clamping force to said one of the two longitudinal rods via a clamping tooth when said one of the two longitudinal rods is received in the rod receptacle and at the same time or with a time offset fixes an angular position of the angular bearing between the clamping head and the cross strut,
   wherein the clamping tooth is pivotably mounted about a pivot axis via a rocker bearing,
   wherein the rocker bearing is configured as a floating bearing,
   wherein the floating bearing permits a pivoting movement and a lateral movement of the pivot axis, and
   wherein the lateral movement is generated due to the clamping force, the clamping tooth acting by redirecting a flow of force in a fixing and/or locking manner on the angular position of the angular bearing between the clamping head and the cross strut.

2. The medical cross connector according to claim 1, wherein the angular bearing is configured to be polyaxial so that the angular position of the angular bearing can be changed and/or fixed in at least two axial directions.

3. The medical cross connector according to claim 2, wherein the angular bearing is in the form of a ball joint connection between the clamping head and the cross strut.

4. The medical cross connector according to claim 2, wherein the angular bearing is configured to be preloaded and/or preloadable by a spring element.

5. The medical cross connector according to claim 4, wherein the spring element is a tension and/or compression spring integrally formed in a component inside the clamping head.

6. The medical cross connector according to claim 5, wherein the component inside the clamping head is an intermediate element configured as a U-shaped fork mount.

7. The medical cross connector according to claim 6, wherein the spring element is arranged to cause a preceding snap onto said one of the two longitudinal rods for clamping said one of the two longitudinal rods.

8. The medical cross connector according to claim 1, wherein the clamping screw is screwable in a reversibly releasable and/or in a self-locking manner.

9. The medical cross connector according to claim 1, wherein the clamping tooth is adjustable and/or adjusted to be differently shaped and/or dimensioned to accommodate a longitudinal rod diameter.

10. The medical cross connector according to claim 9, wherein the clamping tooth is adjustable to accommodate a longitudinal rod diameter of 3 to 7 mm in a cervical or neck region and/or 5.5 to 6.0 mm in a lumbar or lumbar vertebrae region.

11. The medical cross connector according to claim 9, wherein the clamping head is configured such that different clamping teeth can be set up in the clamping head in a modular fashion.

12. The medical cross connector according to claim 1, wherein the lateral movement occurs along a path in the clamping head.

13. The medical cross connector according to claim 12, wherein the path is determined by an elongated hole.

14. The medical cross connector according to claim 12, wherein the path is determined by an elongated hole provided within the clamping head.

15. The medical cross connector according to claim 1, wherein the flow of force is transmitted via an intermediate element of the clamping head.

16. The medical cross connector according to claim 1, wherein the clamping screw is configured to:
   in a first force flow phase, rotate the clamping tooth as a first clamping means in a direction towards said one of the two longitudinal rods about the pivot axis of the clamping tooth as a first axis of rotation until clamping of said one of the two longitudinal rods is achieved along a contact line between the clamping tooth and said one of the two longitudinal rods; and then,
   in a second force flow phase, rotate the clamping tooth about the contact line as a second axis of rotation by its further actuation to move the pivot axis in a direction away from said one of the two longitudinal rods along a path length being configured in the clamping head to permit and/or represent a lateral movement of the rocker bearing.

17. The medical cross connector according to claim 1, wherein a component or an element of the cross connector is made of a biocompatible material and/or of ceramic and/or of a titanium alloy.

18. A medical product set comprising a medical cross connector according to claim 9, in combination with a longitudinal rod.

19. A medical cross connector comprising:
   a cross strut for connecting two longitudinal rods configured for operative engagement for orientation of vertebrae of a spinal column; and
   a clamping head mounted pivotably on the cross strut in an angular bearing and having a trough-shaped rod receptacle and a clamping screw,
   wherein the rod receptacle is configured to receive one of the two longitudinal rods in the rod receptacle,
   wherein the clamping screw, when actuated, applies a clamping force to said one of the two longitudinal rods via a clamping tooth when said one of the two longitudinal rods is received in the rod receptacle and at the same time or with a time offset fixes an angular position of the angular bearing between the clamping head and the cross strut,
   wherein the clamping tooth is pivotably mounted about a pivot axis via a rocker bearing,
   wherein the rocker bearing is configured as a floating bearing,
   wherein the floating bearing permits a pivoting movement and a lateral movement of the pivot axis, and
   wherein the lateral movement is generated due to the clamping force, the clamping tooth acting by redirecting a flow of force in a fixing and/or locking manner on the angular position of the angular bearing between the clamping head and the cross strut,
   wherein the flow of force is transmitted via an intermediate element of the clamping head, and
   wherein the intermediate element of the clamping head is a U-shaped fork mount.

20. The medical cross connector according to claim 19, wherein the clamping tooth is pivotably mounted by a cylinder pin enclosed in two cylinder bores on opposite sides of the U-shaped fork mount,
   wherein the fork mount is movably arranged on an outside of a pressing element of the clamping tooth inside the clamping head, and
   wherein the clamping tooth is enclosed in the U-shaped fork mount on a front side facing towards the rod receptacle and facing away from the angular bearing.

21. A medical cross connector comprising:
   a cross strut for connecting two longitudinal rods configured for operative engagement for orientation of vertebrae of a spinal column; and
   a clamping head mounted pivotably on the cross strut in an angular bearing and having a trough-shaped rod receptacle and a clamping screw,
   wherein the rod receptacle is configured to receive one of the two longitudinal rods in the rod receptacle,
   wherein the clamping screw, when actuated, applies a clamping force to said one of the two longitudinal rods via a clamping tooth when said one of the two longitudinal rods is received in the rod receptacle and at the same time or with a time offset fixes an angular position of the angular bearing between the clamping head and the cross strut,
   wherein the clamping tooth is pivotably mounted about a pivot axis via a rocker bearing,
   wherein the rocker bearing is configured as a floating bearing,
   wherein the floating bearing permits a pivoting movement and a lateral movement of the pivot axis, and
   wherein the lateral movement is generated due to the clamping force, the clamping tooth acting by transferring a flow of force in a fixing and/or locking manner to the angular bearing to fix and/or lock the clamping head to the cross strut.

* * * * *